United States Patent
Diederich et al.

(10) Patent No.: US 10,287,280 B2
(45) Date of Patent: May 14, 2019

(54) CRYSTALLINE FORMS OF (S)-5-BENZYL-N-(5-METHYL-4-OXO-2,3,4,5-TETRAHYDROBENZO[B][1,4]OXAZEPIN-3-YL)-4H-1,2,4-TRIAZOLE-3-CARBOXAMIDE

(71) Applicant: GlaxoSmithKline Intellectual Property Development Limited, Brentford, Middlesex (GB)

(72) Inventors: Ann Marie Diederich, Research Triangle Park, NC (US); Robert Herrmann, King of Prussia, PA (US)

(73) Assignee: GlaxoSmithKline Intellectual Property Development Limited, Brentford, Middlesex (GB)

(*) Notice: Subject to any disclaimer, the term of this patent is extended or adjusted under 35 U.S.C. 154(b) by 0 days.

(21) Appl. No.: 15/548,500

(22) PCT Filed: Feb. 12, 2016

(86) PCT No.: PCT/IB2016/050755
§ 371 (c)(1),
(2) Date: Aug. 3, 2017

(87) PCT Pub. No.: WO2016/128936
PCT Pub. Date: Aug. 18, 2016

(65) Prior Publication Data
US 2018/0022737 A1    Jan. 25, 2018

Related U.S. Application Data

(60) Provisional application No. 62/115,674, filed on Feb. 13, 2015.

(51) Int. Cl.
*C07D 413/12* (2006.01)
*A61K 31/553* (2006.01)
*C07C 223/04* (2006.01)
*C07D 249/10* (2006.01)
*C07D 267/14* (2006.01)

(52) U.S. Cl.
CPC .......... *C07D 413/12* (2013.01); *A61K 31/553* (2013.01); *C07C 223/04* (2013.01); *C07D 249/10* (2013.01); *C07D 267/14* (2013.01); *A61K 2300/00* (2013.01)

(58) Field of Classification Search
CPC .................................................. C07D 413/12
See application file for complete search history.

(56) References Cited

U.S. PATENT DOCUMENTS 9,556,152 B2    1/2017    Harris et al.
9,624,202 B2    4/2017    Jeong et al.

FOREIGN PATENT DOCUMENTS

WO    WO 2014/125444 A1    8/2014

OTHER PUBLICATIONS

Caira: "Crystalline Polymorphism of Organic Compounds". Topics in Current Chemistry, 198:163-208 (Jan. 1, 1998).
Byrn, et al. "Pharmaceutical Solids: A Strategic Approach to Regulatory Considerations". Pharmaceutical Research, 12(7):945-954 (Jul. 1, 1995).
International Search Report, PCT/IB2016/050755, dated Aug. 18, 2016.
Written Opinion, PCT/IB2016/050755, dated Aug. 18, 2016.

*Primary Examiner* — Bruck Kifle
(74) *Attorney, Agent, or Firm* — Kathryn A. Lutomski; Edward R. Gimmi

(57) ABSTRACT

Disclosed are novel crystalline forms of (S)-5-benzyl-N-(5-methyl-4-oxo-2,3,4,5-tetrahydrobenzo[b][1,4]oxazepin-3-yl)-4H-1,2,4-triazole-3-carboxamide, and solvates thereof and pharmaceutical compositions containing the same. Also disclosed are processes for the preparation thereof and methods for use thereof.

19 Claims, 12 Drawing Sheets

CRYSTALLINE FORMS OF (S)-5-BENZYL-N-(5-METHYL-4-OXO-2,3,4,5-TETRAHYDROBENZO[B][1,4]OXAZEPIN-3-YL)-4H-1,2,4-TRIAZOLE-3-CARBOXAMIDE

This application is a § 371 of International Application No. PCT/IB2016/050755, filed 12 Feb. 2016, which claims the benefit of U.S. Provisional Application No. 62/115,674, filed 13 Feb. 2015, which are incorporated herein in their entireties.

FIELD OF THE INVENTION

The present invention relates to novel crystalline forms of (S)-5-benzyl-N-(5-methyl-4-oxo-2,3,4,5-tetrahydrobenzo[b][1,4]oxazepin-3-yl)-4H-1,2,4-triazole-3-carboxamide.

BACKGROUND OF THE INVENTION

International Publication No. WO 2014/125444 (corresponding to U.S. Patent Application Publication No. US 2015/0353533 A1) describes a series of compounds which are inhibitors of RIP1, and which are useful in the treatment of RIP1-mediated disorders. Specifically disclosed is (S)-5-benzyl-N-(5-methyl-4-oxo-2,3,4,5-tetrahydrobenzo[b][1,4]oxazepin-3-yl)-4H-1,2,4-triazole-3-carboxamide. Identification of stable, crystalline forms of such compound would be highly desirable for providing that compound in a form suitable for use in the treatment of RIP1-mediated diseases and disorders, specifically, suitable for administration to a human in need thereof.

SUMMARY OF THE INVENTION

The present invention relates to crystalline forms of the compound: (S)-5-benzyl-N-(5-methyl-4-oxo-2,3,4,5-tetrahydrobenzo[b][1,4]oxazepin-3-yl)-4H-1,2,4-triazole-3-carboxamide (hereinafter "Compound A"), wherein the crystalline forms are crystalline forms of solvates of Compound A.

Specific crystalline solvates of Compound A of this invention are $(C_1-C_4)$alkyl-acetate, $(C_1-C_3)$alkyl-alcohol, methoxy-cyclopentane, methyl-tetrahydrofuran and water (hydrate) solvates. Other crystalline solvates of Compound of A are mixed solvates, such as a hydrate form of other solvates, such as a $(C_1-C_3)$alkyl-alcohol-water solvate. More specifically, this invention is directed to the crystalline methyl acetate, ethyl acetate, n-propyl acetate, isopropyl acetate, water, ethanol, iso-propyl alcohol, methyl-isobutylketone, 2-methyl-tetrahydrofuran, dimethyl carbonate, and methoxy-cyclopentane solvate forms of Compound A.

Compound A is represented by Structure (I):

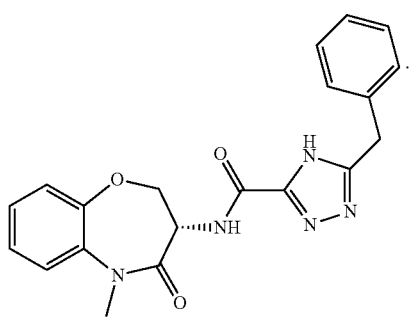

(I)

Compound A may be useful for inhibiting RIP1, and for treating diseases such as inflammatory bowel disease, including Crohn's disease and ulcerative colitis. Compound A may also be useful for treating diseases such as psoriasis and rheumatoid arthritis and for treatment of burn injuries.

DETAILED DESCRIPTION OF THE INVENTION

As illustrated above, (S)-5-benzyl-N-(5-methyl-4-oxo-2,3,4,5-tetrahydrobenzo[b][1,4]oxazepin-3-yl)-4H-1,2,4-triazole-3-carboxamide, or Compound A is present in the crystalline forms of this invention as a free base, that is, a non-salt form. Accordingly, the term "Compound A" is intended to represent (S)-5-benzyl-N-(5-methyl-4-oxo-2,3,4,5-tetrahydrobenzo[b][1,4]oxazepin-3-yl)-4H-1,2,4-triazole-3-carboxamide (free base).

Described herein is an anhydrous crystalline form (Form 1) of Compound A (hereinafter, Compound A-Form 1) wherein the crystalline form is characterized by an X-ray powder diffraction (XRPD) pattern substantially in accordance with FIG. 1. Also described is Compound A-Form 1, characterized by diffraction data substantially in accordance with Table 1.

It has been discovered that Compound A will from crystalline solvates with a variety of solvents. Specific crystalline solvates of Compound A of this invention are $(C_1-C_4)$alkyl-acetate, $(C_1-C_3)$alkyl-alcohol, methoxy-cyclopentane, methyl-tetrahydrofuran and water (hydrate) solvates. Other crystalline solvates of Compound of A are mixed solvates, such as a hydrate form of other solvates, such as a $(C_1-C_3)$alkyl-alcohol-water solvate.

Accordingly, this invention is directed to crystalline solvate forms of Compound A. Specifically, this invention is directed to the crystalline methyl acetate, ethyl acetate, n-propyl acetate, isopropyl acetate, water, ethanol, iso-propyl alcohol, methyl-isobutylketone, 2-methyl-tetrahydrofuran, dimethyl carbonate, and methoxy-cyclopentane solvate forms of Compound A.

Figure 2:
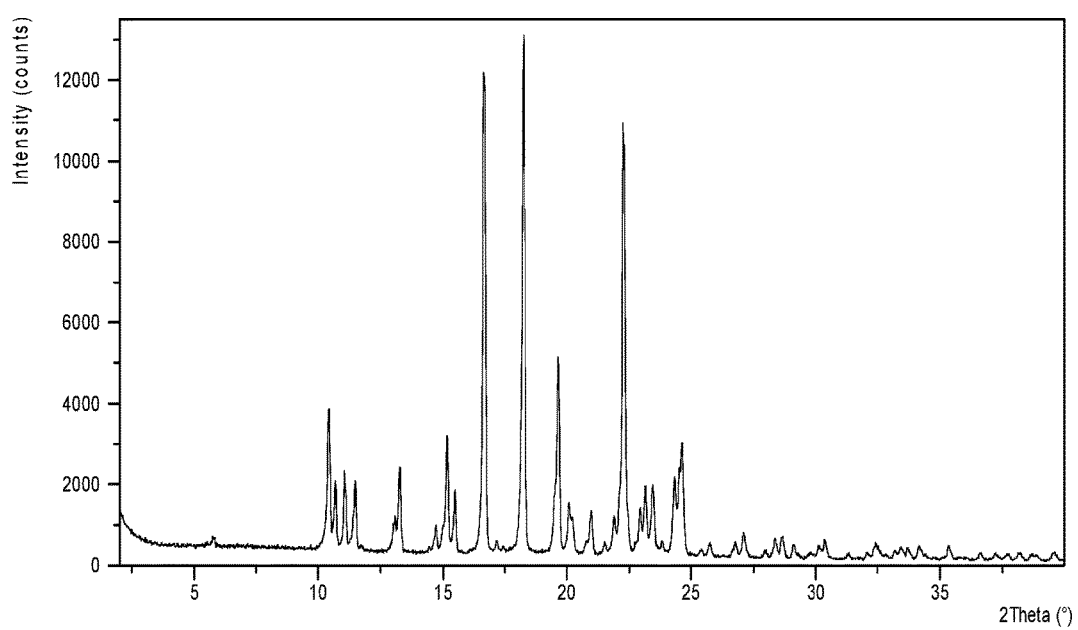
FIG. 2 shows an X-ray powder diffraction pattern of the methyl acetate solvate of Compound A.

Thus, in one embodiment, this invention is directed to Compound A—methyl acetate solvate, wherein the crystalline form is characterized by an XRPD pattern substantially in accordance with FIG. 2. This invention is also directed to Compound A—methyl acetate solvate, wherein the crystalline form is characterized by diffraction data substantially in accordance with Table 2.

Figure 3:
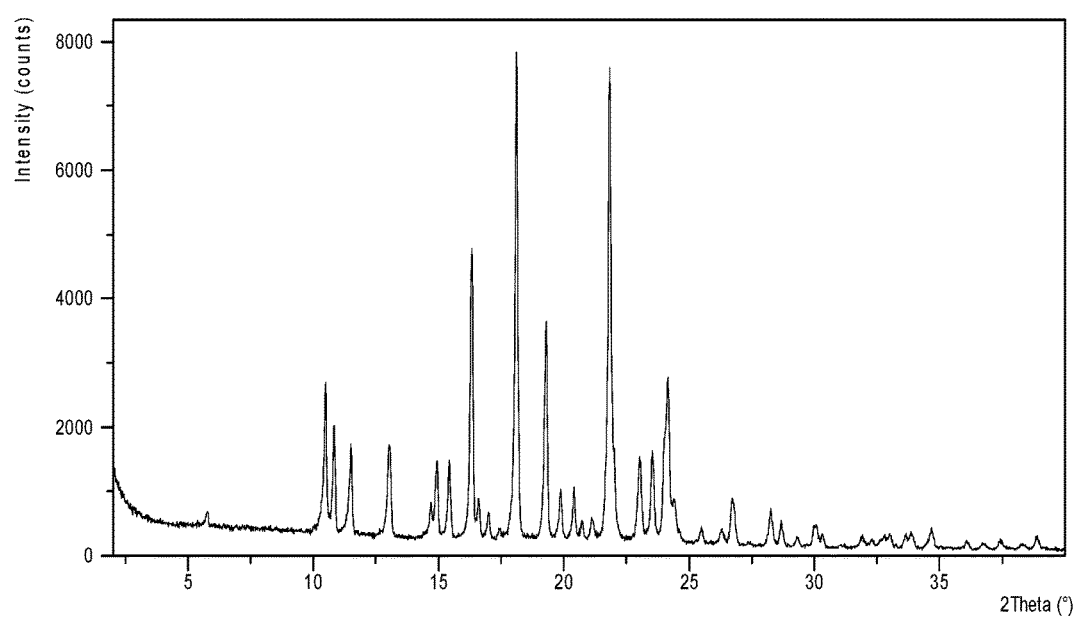
FIG. 3 shows an X-ray powder diffraction pattern of the ethyl acetate solvate of Compound A.

Another embodiment of the present invention is directed to Compound A—ethyl acetate solvate, wherein the crystalline form is characterized by an XRPD pattern substantially in accordance with FIG. 3. This invention is also directed to Compound A—ethyl acetate solvate, wherein the crystalline form is characterized by diffraction data substantially in accordance with Table 3.

Figure 4:
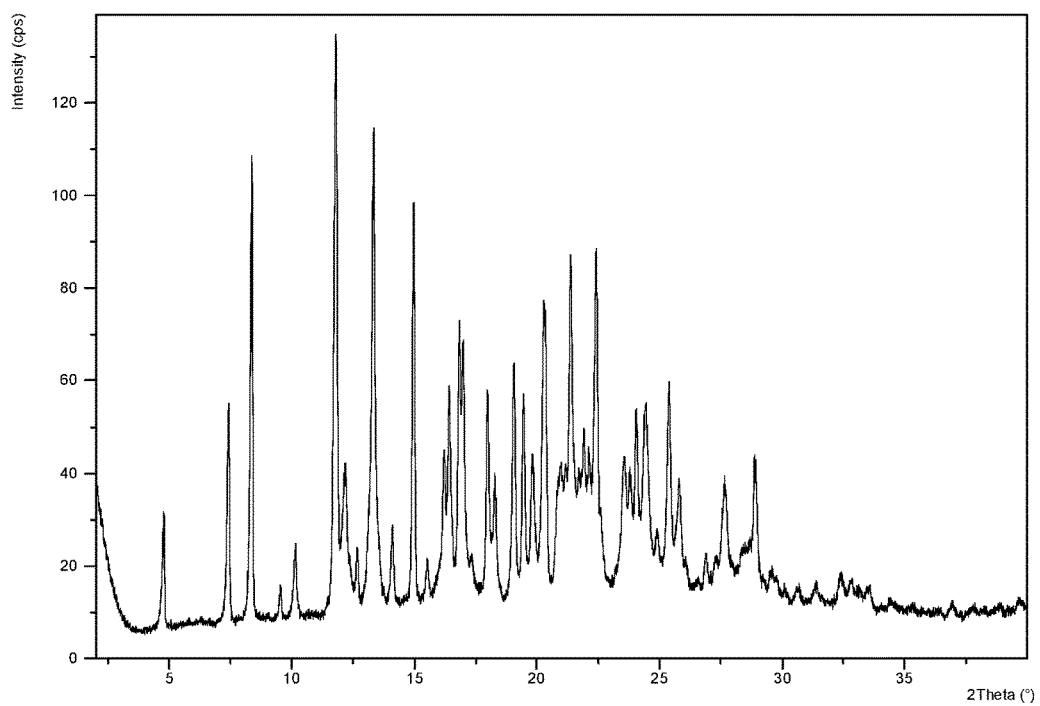
FIG. 4 shows an X-ray powder diffraction pattern of the n-propyl acetate solvate of Compound A.

Another embodiment of the present invention is directed to Compound A—n-propyl acetate solvate, wherein the crystalline form is characterized by an XRPD pattern substantially in accordance with FIG. 4. This invention is also directed to Compound A—n-propyl acetate solvate, wherein the crystalline form is characterized by diffraction data substantially in accordance with Table 4.

Figure 5:
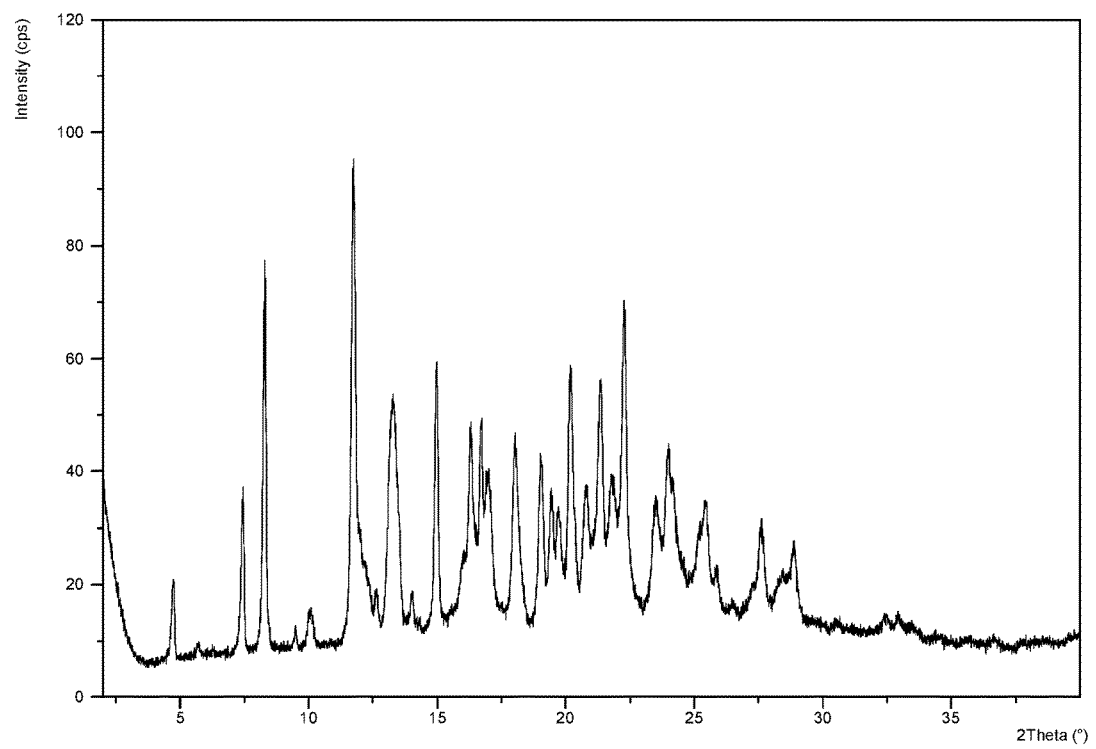
FIG. 5 shows an X-ray powder diffraction pattern of the isopropyl acetate solvate of Compound A.

Another embodiment of the present invention is directed to Compound A—isopropyl acetate solvate, wherein the crystalline form is characterized by an XRPD pattern substantially in accordance with FIG. 5. This invention is also directed to Compound A—isopropyl acetate solvate, wherein the crystalline form is characterized by diffraction data substantially in accordance with Table 5.

Figure 6:
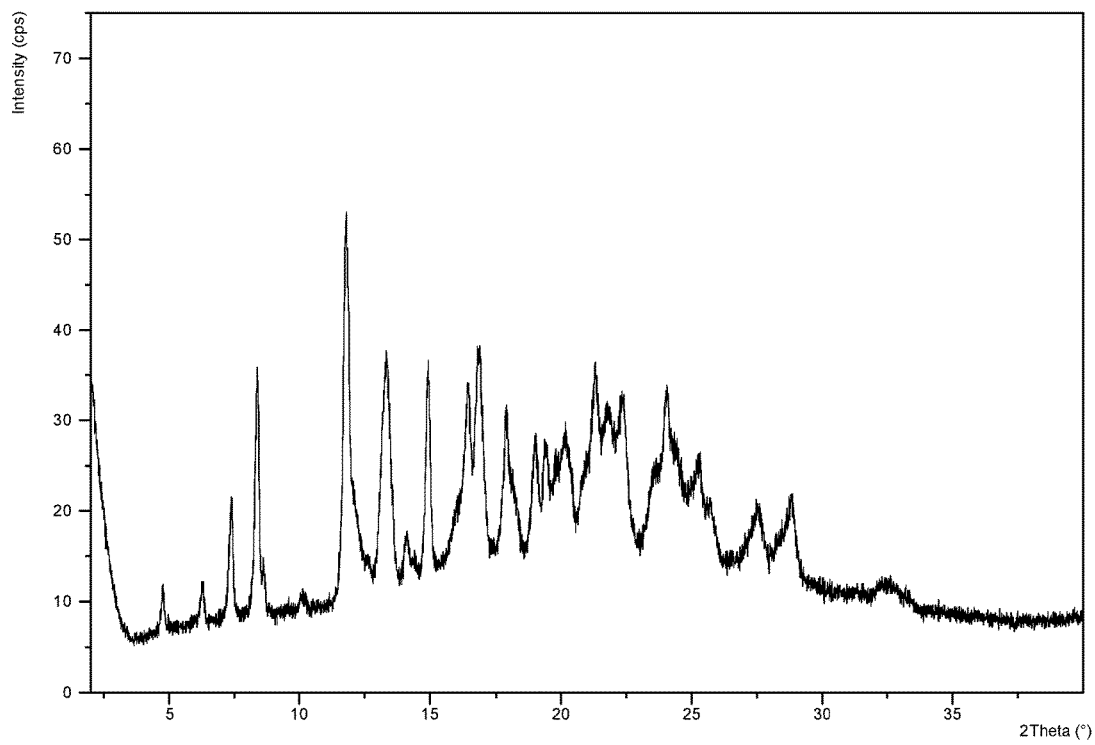
FIG. 6 shows an X-ray powder diffraction pattern of the ethanol solvate of Compound A.

Another embodiment of the present invention is directed to Compound A—ethanol solvate, wherein the crystalline form is characterized by an XRPD pattern substantially in accordance with FIG. 6. This invention is also directed to Compound A—ethanol solvate, wherein the crystalline form is characterized by diffraction data substantially in accordance with Table 6.

Figure 7:
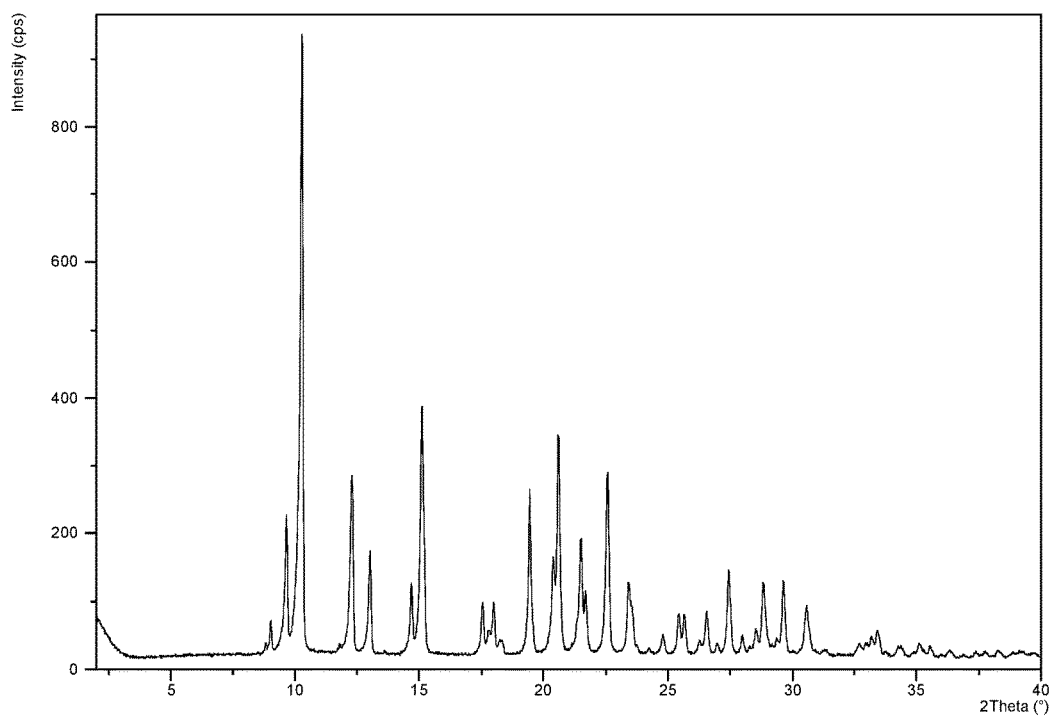
FIG. 7 shows an X-ray powder diffraction pattern of Compound A monohydrate.

Another embodiment of the present invention is directed to Compound A monohydrate, wherein the crystalline form is characterized by an XRPD pattern substantially in accordance with FIG. 7. This invention is also directed to Compound A—monohydrate, wherein the crystalline form is characterized by diffraction data substantially in accordance with Table 7.

Figure 8:
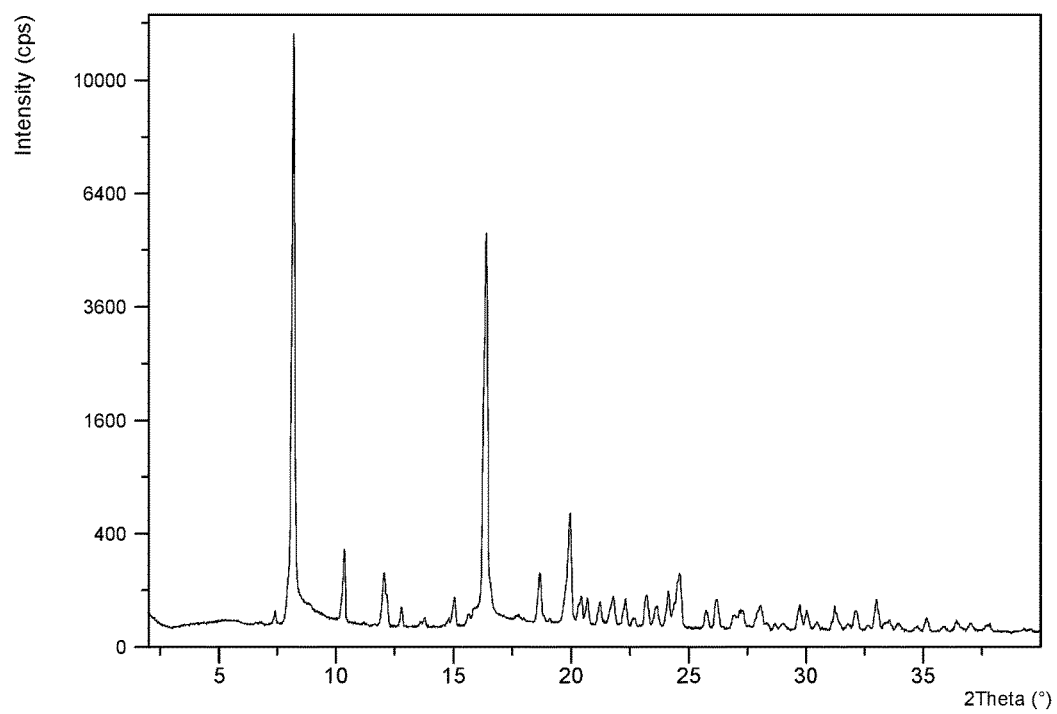
FIG. 8 shows an X-ray powder diffraction pattern of the isopropyl alcohol solvate of Compound A.

Another embodiment of the present invention is directed to Compound A—isopropyl alcohol solvate, wherein the crystalline form is characterized by an XRPD pattern substantially in accordance with FIG. 8. This invention is also directed to Compound A—isopropyl alcohol solvate, wherein the crystalline form is characterized by diffraction data substantially in accordance with Table 8.

Figure 9:
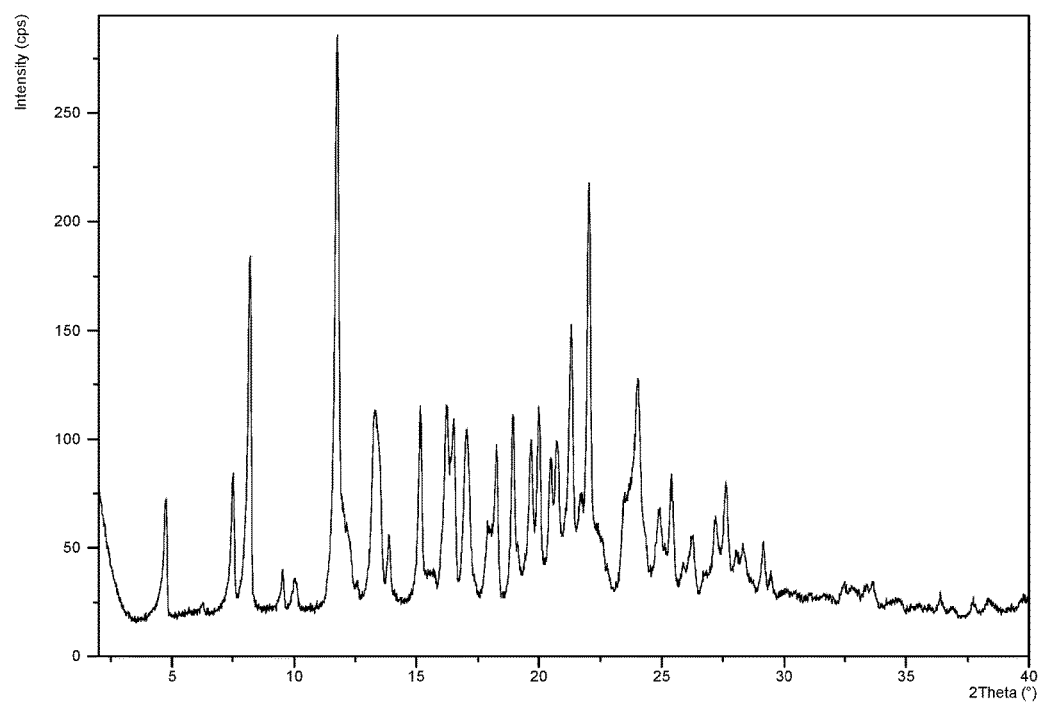
FIG. 9 shows an X-ray powder diffraction pattern of the methyl-isobutyl ketone solvate of Compound A.

Another embodiment of the present invention is directed to Compound A—methyl-isobutyl ketone solvate, wherein the crystalline form is characterized by an XRPD pattern substantially in accordance with FIG. 9. This invention is also directed to Compound A—methyl-isobutyl ketone solvate, wherein the crystalline form is characterized by diffraction data substantially in accordance with Table 9.

Figure 10:
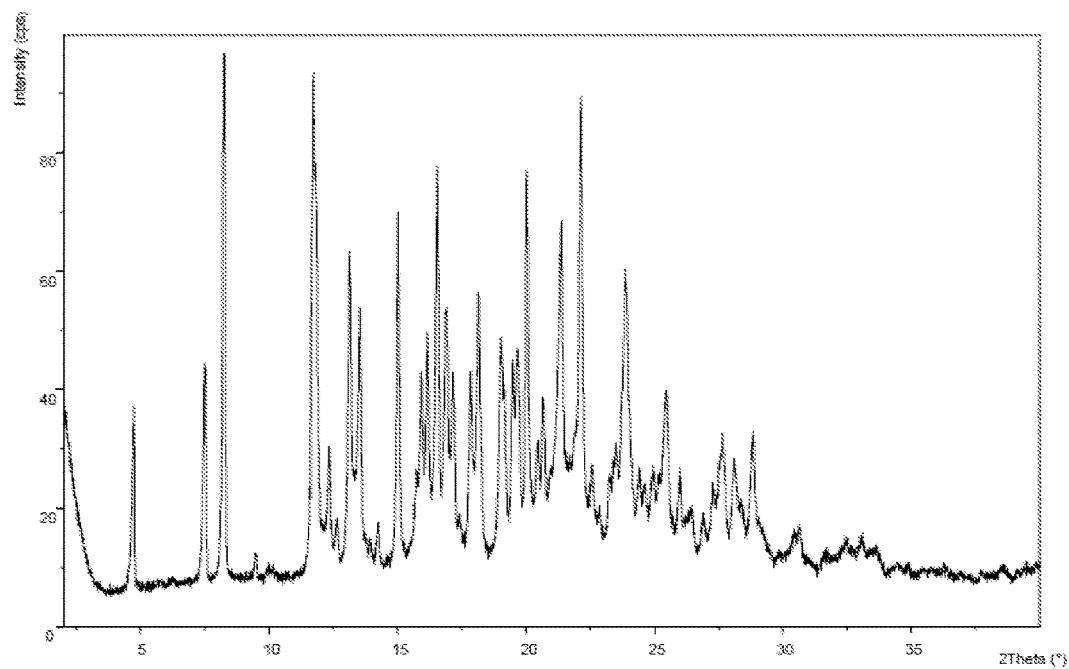
FIG. 10 shows an X-ray powder diffraction pattern of the 2-methyl-tetrahydrofuran solvate of Compound A.

Another embodiment of the present invention is directed to Compound A—2-methyl-tetrahydrofuran solvate, wherein the crystalline form is characterized by an XRPD pattern substantially in accordance with FIG. 10. This invention is also directed to Compound A—2-methyl-tetrahydrofuran solvate, wherein the crystalline form is characterized by diffraction data substantially in accordance with Table 10.

Figure 11:
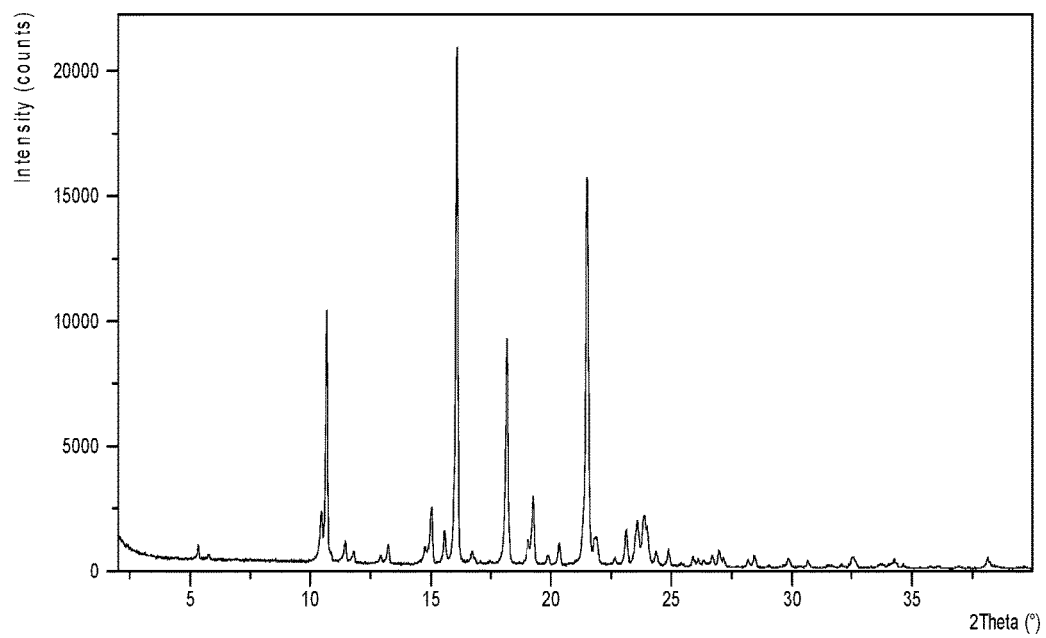
FIG. 11 shows an X-ray powder diffraction pattern of the dimethyl carbonate solvate of Compound A.

Another embodiment of the present invention is directed to Compound A—dimethyl carbonate solvate, wherein the crystalline form is characterized by an XRPD pattern substantially in accordance with FIG. 11. This invention is also directed to Compound A—dimethyl carbonate solvate, wherein the crystalline form is characterized by diffraction data substantially in accordance with Table 11.

Figure 12:
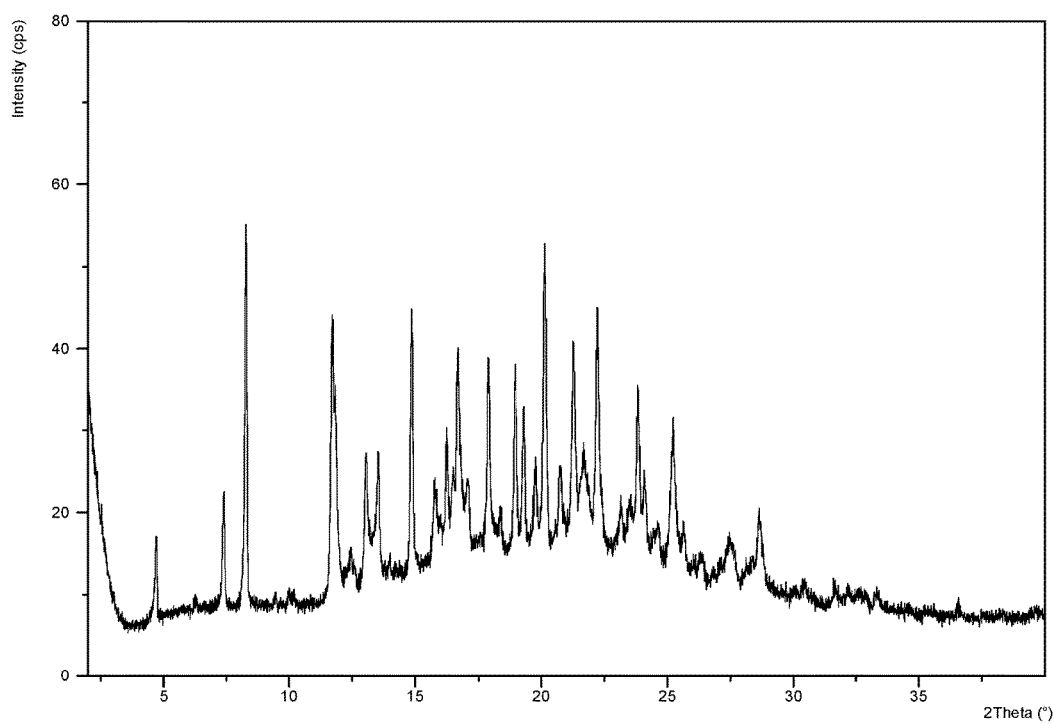
FIG. 12 shows an X-ray powder diffraction pattern of the methoxy-cyclopentane solvate of Compound A.

Another embodiment of the present invention is directed to Compound A—methoxy-cyclopentane solvate, wherein the crystalline form is characterized by an XRPD pattern substantially in accordance with FIG. 12. This invention is also directed to Compound A—methoxy-cyclopentane solvate, wherein the crystalline form is characterized by diffraction data substantially in accordance with Table 12.

Because of their potential use in medicine, the crystalline forms of Compound A are preferably pharmaceutically acceptable crystalline forms. Such pharmaceutically acceptable crystalline forms include solvated and non-solvated forms. Accordingly, Compound A-Form 1 is a pharmaceutically acceptable crystalline form of Compound A.

The solvents associated with the pharmaceutically acceptable crystalline solvate forms of Compound A are pharmaceutically acceptable. The International Conference on Harmonisation of Technical Requirements for Registration of Pharmaceuticals for Human Use (ICH) guidance for industry *Q3C Impurities: Residual Solvents* (1997), makes recommendations as to what amounts of residual solvents are considered safe in pharmaceuticals. The term "permitted daily exposure" (PDE) is defined as a pharmaceutically acceptable intake of residual solvents. Residual solvents were assessed for their possible risk to human health and placed into one of three classes as follows:

Class 1 solvents: Solvents to be avoided; known human carcinogens, strongly suspected human carcinogens, and environmental hazards;

Class 2 solvents: Solvents to be limited; non-genotoxic animal carcinogens or possible causative agents of other irreversible toxicity such as neurotoxicity or teratogenicity; solvents suspected of other significant but reversible toxicities;

Class 3 solvents: Solvents with low toxic potential; solvents with low toxic potential to man; no health-based exposure limit is needed. Class 3 solvents have PDEs of 50 mg or more per day.

A separate group of Class 4 solvents has been created for solvents for which no adequate toxicological data were found. These are solvents for which no adequate toxicological data on which to base a PDE were found.

It is generally accepted that the solvents present in pharmaceutically acceptable solvates include those solvents of Class 3. Of the solvates described herein, methyl acetate, ethyl acetate, n-propyl acetate, isopropyl acetate, ethanol, water, methyl-isobutyl ketone, and iso-propyl alcohol are Class 3 solvents. Accordingly, the methyl acetate, ethyl acetate, n-propyl acetate, isopropyl acetate, ethanol, water, methyl-isobutyl ketone, and iso-propyl alcohol solvates may be generally considered to be pharmaceutically acceptable solvates.

It may be possible for solvents in Class 4 to be pharmaceutically acceptable. Of the solvates described herein, 2-methyl-tetrahydrofuran is a Class 4 solvent.

As used herein, the term "compound of the invention" means a crystalline form of Compound A, characterized by the XRPD patterns substantially in accordance with FIGS. 1-12 and/or the diffraction data substantially in accordance with Tables 1-12. When used with regard to use in therapy or a method of treatment, the term "compound of the invention" refers to a pharmaceutically acceptable crystalline form of Compound A. Mixtures of compounds of the invention, or mixtures of pharmaceutically acceptable crystalline forms of Compound A, may include, for example, a mixture of Compound A-Form 1 and Compound A, monohydrate.

Figure 1:
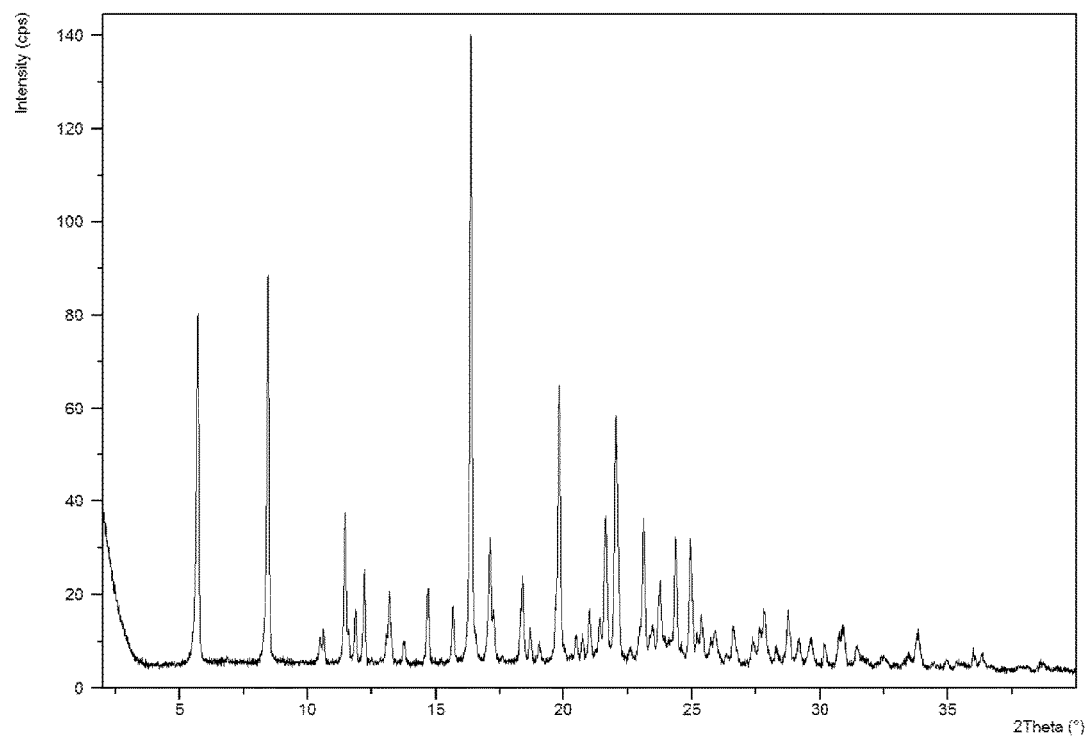
FIG. 1 shows an X-ray powder diffraction pattern of Compound A-Form 1.

One pharmaceutically acceptable crystalline form of Compound A is crystalline Compound A-Form 1, characterized by an XRPD pattern substantially in accordance with FIG. 1. Another pharmaceutically acceptable crystalline form of Compound A is crystalline Compound A-Form 1, characterized by diffraction data substantially in accordance with Table 1.

Other pharmaceutically acceptable crystalline forms of Compound A may include the methyl acetate, ethyl acetate, n-propyl acetate, isopropyl acetate, ethanol, water, iso-propyl alcohol and methyl-isobutyl ketone crystalline solvates of Compound A, characterized by an XRPD patterns substantially in accordance with FIGS. 2-9 and/or the diffraction data substantially in accordance with Tables 2-9.

It is well known and understood to those skilled in the art that the apparatus employed, humidity, temperature, orientation of the powder crystals, and other parameters involved in obtaining an XRPD pattern may cause some variability in the appearance, intensities, and positions of the lines in the diffraction pattern. An X-ray powder diffraction pattern that is "substantially in accordance" with that of the Figures provided herein is an XRPD pattern that would be considered by one skilled in the art to represent a compound possessing the same crystal form as the compound that provided the XRPD pattern of the Figures. For example, the XRPD pattern may be identical to that of FIG. 1, or more likely it may be somewhat different. Such an XRPD pattern may not necessarily show each of the lines of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns. For example, one skilled in the art can overlay an XRPD pattern of a sample of a crystalline Compound A with FIG. 1, and using expertise and knowledge in the art, readily determine whether the XRPD pattern of the sample is substantially in accordance with the XRPD pattern of Compound A—Form 1. If the XRPD pattern is substantially in accordance with FIG. 1, the sample form can be readily and accurately identified as having the same form as Compound A—Form 1. Similarly, a person skilled in the art is capable of determining if a given diffraction angle (expressed in °2θ) obtained from an XRPD pattern is at about the same position as a recited value.

Compound A may be particularly useful for the treatment of RIP1 kinase-mediated diseases or disorders. Such RIP1 kinase-mediated diseases or disorders are diseases or disorders that are mediated by activation of RIP1 kinase, and as such, are diseases or disorders where inhibition of RIP1 kinase would provide benefit. The compounds of the invention may be particularly useful for the treatment of diseases/disorders which are likely to be regulated at least in part by programmed necrosis, apoptosis or the production of inflammatory cytokines, particularly inflammatory bowel disease (including Crohn's disease and ulcerative colitis), psoriasis, retinal detachment, retinitis pigmentosa, macular degeneration, pancreatitis, atopic dermatitis, arthritis (including rheumatoid arthritis, spondyloarthritis, gout, systemic onset juvenile idiopathic arthritis (SoJIA), psoriatic arthritis), systemic lupus erythematosus (SLE), Sjogren's syndrome, systemic scleroderma, anti-phospholipid syndrome (APS), vasculitis, osteoarthritis, liver damage/diseases (non-alcohol steatohepatitis, alcohol steatohepatitis, autoimmune hepatitis, autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury(AKI)) Celiac disease, autoimmune idiopathic thrombocytopenic purpura (autoimmune ITP), transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, Amyotrophic lateral sclerosis (ALS), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), peridontitis, NEMO-deficiency syndrome (NF-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2 Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease).

The treatment of the above-noted diseases/disorders may concern, more specifically, the amelioration of organ injury or damage sustained as a result of the noted diseases. For example, the compounds of this invention may be particularly useful for amelioration of brain tissue injury or damage following ischemic brain injury or traumatic brain injury, or for amelioration of heart tissue injury or damage following myocardial infarction, or for amelioration of brain tissue injury or damage associated with Huntington's disease, Alzheimer's disease or Parkinson's disease, or for amelioration of liver tissue injury or damage associated with non-alcohol steatohepatitis, alcohol steatohepatitis, autoimmune hepatitis autoimmune hepatobiliary diseases, or primary sclerosing cholangitis. In addition, the treatment of diseases/disorders selected from those described herein may concern, more specifically, the amelioration of liver tissue injury or damage associated with overdose of acetaminophen, or for amelioration of kidney tissue injury or damage following renal transplant or the administration of nephrotoxic drugs or substances e.g. cisplatin.

Compound A may be particularly useful for the treatment of inflammatory bowel disease (including Crohn's disease and ulcerative colitis), psoriasis, retinal detachment, retinitis pigmentosa, arthritis (including rheumatoid arthritis, spondyloarthritis, gout, and systemic onset juvenile idiopathic arthritis (SoJIA)), transplant rejection, and/or ischemia reperfusion injury of solid organs. Compound A may also be useful for treatment of burn injuries.

Treatment of RIP 1-mediated disease conditions, or more broadly, treatment of immune mediated disease, may be achieved using Compound A as a monotherapy, or in dual or multiple combination therapy, particularly for the treatment of refractory cases, such as in combination with other anti-inflammatory and/or anti-TNF agents, which may be administered in therapeutically effective amounts as is known in the art.

Compound A may be employed alone or in combination with other therapeutic agents. Combination therapies thus comprise the administration of at least one pharmaceutically acceptable crystalline form of Compound A and at least one other therapeutically active agent. Compound A and the other therapeutically active agent(s) may be administered together in a single pharmaceutical composition or separately and, when administered separately this may occur simultaneously or sequentially in any order. The amounts of Compound A and the other therapeutically active agent(s) and the relative timings of administration will be selected in order to achieve the desired combined therapeutic effect. Thus in a further aspect, there is provided a combination comprising a pharmaceutically acceptable crystalline form of Compound A together with one or more other therapeutically active agents. In one aspect, there is provided a combination comprising a pharmaceutically acceptable crystalline form of Compound A, characterized by the XRPD pattern of any one of FIGS. 1-9, together with one or more other therapeutically active agents. In another aspect, there is provided a combination comprising a pharmaceutically acceptable crystalline form of Compound A, characterized by the diffraction data of any one of Tables 1-9, together with one or more other therapeutically active agents. Thus in one aspect of this invention, a pharmaceutically acceptable crystalline form of Compound A, or a pharmaceutical composition comprising a pharmaceutically acceptable crystalline form of Compound A may be used in combination with or include one or more other therapeutic agents, for example an anti-inflammatory agent and/or an anti-TNF agent.

For example, Compound A may be administered in combination with other anti-inflammatory agents for any of the indications above, including oral or topical corticosteroids (such as prednisone (Deltasone®) and bundesonide), anti-TNF agents (including anti-TNF biologic agents), 5-aminosalicyclic acid and mesalamine preparations, hydroxycloroquine, thiopurines (azathioprin, mercaptopurin), methotrexate, cyclophosphamide, cyclosporine, calcineurin inhibitors (cyclosporine, pimecrolimus, tacrolimus), mycophenolic acid (CellCept®), mTOR inhibitors (temsirolimus, everolimus), JAK inhibitors (tofacitinib), (Xeljan®)), Syk inhibitors (fostamatinib), anti-IL6 biologics, anti-IL1 (anakinra (Kineret®), canakinumab (Ilaris®), rilonacept (Arcalyst®)), anti-IL12 and IL23 biologics (ustekinumab(Stelara®)), anti-IL17 biologics (secukinumab), anti-CD22 (epratuzumab), anti-integrin agents(natalizumab (Tysabri®)), vedolizumab (Entyvio®)), anti-IFNa (sifalimumab), anti-CD20 or CD4 biologics and other cytokine inhibitors or biologics to T-cell or B-cell receptors or interleukins.

Examples of suitable anti-inflammatory biologic agents include Actemra® (anti-IL6R mAb), anti-CD20 mAbs (rituximab (Rituxan®) and ofatumumab (Arzerra®)), abatacept (Orencia®), anakinra (Kineret®), ustekinumab (Stelara®), and belimumab (Benlysta®). Examples of other suitable anti-inflammatory biologic agents include Canakinumab (Ilaris®), rilonacept (Arcalyst®), secukinumab, epratuzumab, sifalimumab, and ustekinumab (Stelara®). Examples of suitable anti-TNF agents biologic agents include etanecerpt (Enbrel®), adalimumab (Humira®), infliximab (Remicade®), certolizumab (Cimzia®), and golimumab (Simponi®).

Accordingly, one embodiment of this invention is directed to a method of treating a RIP1 kinase-mediated disease or disorder comprising administering a therapeutically effective amount of a pharmaceutically acceptable crystalline form of Compound A to a human in need thereof. In another embodiment, this invention is directed to a method of treating a RIP1 kinase-mediated disease or disorder (specifically, a disease or disorder recited herein) comprising administering a therapeutically effective amount of a pharmaceutically acceptable crystalline form of Compound A, characterized by the XRPD pattern of any one of FIGS. 1-9, to a human in need thereof. This invention is also directed to a method of treating a RIP1 kinase-mediated disease or disorder (specifically, a disease or disorder recited herein) comprising administering a therapeutically effective amount of a pharmaceutically acceptable crystalline form of Compound A, characterized by the diffraction data of any one of Tables 1-9, to a human in need thereof.

Specifically, this invention provides a pharmaceutically acceptable crystalline form of Compound A for use in therapy. More specifically, this invention provides a pharmaceutically acceptable crystalline form of Compound A, as characterized by the XRPD pattern of any one of FIGS. 1-9, for use in therapy. This invention also provides for a pharmaceutically acceptable crystalline form of Compound A, as characterized by the diffraction data of any one of Tables 1-9, for use in therapy.

In another embodiment, this invention provides a pharmaceutically acceptable crystalline form of Compound A for use in the treatment of a RIP1 kinase-mediated disease or disorder. More specifically, this invention provides a pharmaceutically acceptable crystalline form of Compound A, as characterized by the XRPD pattern of any one of FIGS. 1-9, for use in the treatment of a RIP1 kinase-mediated disease or disorder, particularly, a disease or disorder recited herein. This invention also provides for a pharmaceutically acceptable crystalline form of Compound A, as characterized by the diffraction data of any one of Tables 1-9, for use in the treatment of a RIP1 kinase-mediated disease or disorder, particularly, a disease or disorder recited herein.

This invention provides for the use of a pharmaceutically acceptable crystalline form of Compound A as an active therapeutic substance. More specifically, this invention provides for the use of a pharmaceutically acceptable crystalline form of Compound A, as characterized by the XRPD pattern of any one of FIGS. 1-9, for the treatment of a RIP1 kinase-mediated disease or disorder, for example, a disease or disorder recited herein. This invention also provides for the use of a pharmaceutically acceptable crystalline form of Compound A, as characterized by the diffraction data of any one of Tables 1-9, for the treatment of a RIP1 kinase-mediated disease or disorder, for example, a disease or disorder recited herein. The invention specifically provides for the use of a pharmaceutically acceptable crystalline form of Compound A as an active therapeutic substance in the treatment of a human in need thereof with a RIP1 kinase-mediated disease or disorder.

The invention further provides for the use of a pharmaceutically acceptable crystalline form of Compound A in the manufacture of a medicament for use in the treatment of a RIP1 kinase-mediated disease or disorder. More specifically, this invention provides for the use of a pharmaceutically acceptable crystalline form of Compound A, as characterized by the XRPD pattern of any one of FIGS. 1-9, in the manufacture of a medicament for use in the treatment of a RIP 1 kinase-mediated disease or disorder, for example, a disease or disorder recited herein. This invention also provides for the use of a pharmaceutically acceptable crystalline form of Compound A, as characterized by the diffraction data of any one of Tables 1-9, in the manufacture of a medicament for use in the treatment of a RIP1 kinase-mediated disease or disorder, for example, a disease or disorder recited herein.

A therapeutically "effective amount" is intended to mean that amount of Compound A that, when administered to a patient in need of such treatment, is sufficient to effect treatment, as defined herein. Thus, e.g., a therapeutically effective amount of a pharmaceutically acceptable crystalline form of Compound A is a quantity of Compound A that when administered to a human in need thereof is sufficient to modulate and/or inhibit the activity of RIP1 kinase such that a disease condition which is mediated by RIP1 is reduced, alleviated or prevented.

For the avoidance of doubt, when a weight/weight range is provided for Compound A (that is, for a pharmaceutically acceptable crystalline form of Compound A disclosed herein), the weight refers to the equivalent weight of Compound A (free base) and does not include the additional weight provided by occluded solvent, if present in the crystalline form.

The amount of the pharmaceutically acceptable crystalline form of Compound A that will correspond to such an amount will vary depending upon factors such as the efficacy, biological half-life, disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of Compound A will vary according to the identity of the mammal in need of treatment (e.g., weight), the particular crystalline form and its properties (e.g., pharmacokinetic properties), disease or disorder and its severity and the specific composition and method being used, but can nevertheless be determined by one of skill in the art.

"Treating" or "treatment" is intended to mean at least the mitigation of a disease or disorder in a patient. The methods of treatment for mitigation of a disease or disorder include the use of the compounds in this invention in any conventionally acceptable manner, for example for prevention, retardation, prophylaxis, therapy or cure of a RIP 1 kinase-mediated disease or disorder, as described hereinabove.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disease or disorder being treated, the severity of the disease or disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Total daily dosages range from 1 mg to 2000 mg of Compound A, preferably, total daily dosages range from 1 mg to 250 mg of Compound A.

For use in therapy, the compounds of the invention will be normally, but not necessarily, formulated into a pharmaceutical composition, or administration unit, prior to administration to a patient. Accordingly, the invention also is directed to a pharmaceutical composition comprising a compound of the invention and one or more pharmaceutically acceptable excipients. The invention also is directed to an administration unit comprising a compound of the invention and one or more pharmaceutically acceptable excipients.

The invention is further directed to a pharmaceutical composition comprising a pharmaceutically acceptable crystalline form of Compound A and one or more pharmaceutically acceptable excipients. The invention is also directed to an administration unit comprising a pharmaceutically acceptable crystalline form of Compound A and one or more pharmaceutically acceptable excipients.

More specifically, this invention is directed to a pharmaceutical composition comprising a pharmaceutically acceptable crystalline form of Compound A, as characterized by the XRPD pattern of any one of FIGS. 1-9, and one or more pharmaceutically acceptable excipients. This invention is also directed to a pharmaceutical composition comprising a pharmaceutically acceptable crystalline form of Compound A, as characterized by the diffraction data of any one of Tables 1-9, and one or more pharmaceutically acceptable excipients.

The pharmaceutical compositions or administration units of the invention may be prepared and packaged in bulk form wherein an effective amount of a compound of the invention can be extracted and then given to the patient such as with powders, syrups, and solutions for injection. Alternatively, the pharmaceutical compositions or administration units of the invention may be prepared and packaged in unit dosage form. For oral application, for example, one or more tablets or capsules may be administered. A dose of the pharmaceutical composition contains at least a therapeutically effective amount of a compound of the invention. When prepared in unit dosage form, the pharmaceutical compositions or administration units may contain from 1 mg to 1000 mg of Compound A.

The administration unit according to the invention comprises a therapeutically effective amount of Compound A, wherein at least 10% by weight of said therapeutically effective amount of Compound A, or at least 30% by weight, or at least 40% by weight, or at least 50% by weight, or at least 60% by weight, or at least 70% by weight, or at least 80% by weight, or at least 90% by weight, or at least 95% by weight, or at least 96% by weight, or at least 97% by weight, or at least 98% by weight, or at least 99% by weight of said therapeutically effective amount of Compound A, is present as a pharmaceutically acceptable crystalline form of Compound A.

The administration unit according to the invention comprises a therapeutically effective amount of Compound A, wherein at least 10% by weight of said therapeutically effective amount of Compound A, or at least 30% by weight, or at least 40% by weight, or at least 50% by weight, or at least 60% by weight, or at least 70% by weight, or at least 80% by weight, or at least 90% by weight, or at least 95% by weight, or at least 96% by weight, or at least 97% by weight, or at least 98% by weight, or at least 99% by weight of said therapeutically effective amount of Compound A, is present as a pharmaceutically acceptable crystalline form of Compound A characterized by the XRPD pattern of any one of FIGS. 1-9.

The administration unit according to the invention comprises a therapeutically effective amount of Compound A, wherein at least 10% by weight of said therapeutically effective amount of Compound A, or at least 30% by weight, or at least 40% by weight, or at least 50% by weight, or at least 60% by weight, or at least 70% by weight, or at least 80% by weight, or at least 90% by weight, or at least 95% by weight, or at least 96% by weight, or at least 97% by weight, or at least 98% by weight, or at least 99% by weight of said therapeutically effective amount of Compound A, is present as a pharmaceutically acceptable crystalline form of Compound A characterized by the diffraction data of any one of Tables 1-9.

The total content of Compound A, as well as the relative content of the pharmaceutically acceptable crystalline form of Compound A, can be determined by standard analysis known to the skilled artisan. Suitable methods include but are not limited to thermal analysis, HPLC and XRPD.

In a preferred embodiment of the administration unit according to the invention, not more than 90% by weight of said therapeutically effective amount of Compound A is non-crystalline (e.g., amorphous). Preferably, not more than 80% by weight, or not more than 70% by weight, or not more than 60% by weight, or not more than 50% by weight, or not more than 40% by weight, or not more than 30% by weight, or not more than 20% by weight, or not more than 10% by weight of said therapeutically effective amount of Compound A is amorphous. Preferably, not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of said therapeutically effective amount of Compound A is amorphous. The total content of amorphous Compound A, as well as the relative content of any one of crystalline Forms 1-9 of Compound A can be determined by standard analysis known to the skilled artisan. Suitable methods include but are not limited to thermal analysis, HPLC and XRPD (see e.g. K. D. Harris, Powder diffraction crystallography of molecular solids, Top Curr. Chem., 2012, 315:133-77; N. Chieng, T. Rades, J.Aaltonen, An overview of recent studies on the analysis of pharmaceutical polymorphs, J Pharm Biomed Anal. 2011, 25:55(4):618-44; R. Hilfiker, Polymorphism, Wiley-VCH, 1st ed. 2006; H. G. Brittain, Polymorphism in Pharmaceutical Solids (Drugs and the Pharmaceutical Sciences), Informa Healthcare, 2nd ed. 2009).

As provided herein, unit dosage forms (pharmaceutical compositions or administration units) containing from 1 mg to 1000 mg of Compound A may be administered one, two, three, or four times per day, preferably one, two, or three times per day, and more preferably, one or two times per day, to effect treatment of a RIP1 kinase-mediated disease or disorder.

The pharmaceutical compositions or administration units of the invention typically contain one pharmaceutically acceptable crystalline form of Compound A. However, in certain embodiments, the pharmaceutical compositions or administration units of the invention contain a mixture of more than one pharmaceutically acceptable crystalline forms of Compound A. In addition, the pharmaceutical compositions or administration units of the invention may optionally further comprise one or more additional pharmaceutically active compounds.

As used herein, "pharmaceutically acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically acceptable.

The compounds of the invention and the pharmaceutically acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company). Accordingly, another embodiment of this invention is a method of preparing a pharmaceutical composition or administration unit comprising the step of admixing a pharmaceutically acceptable crystalline form of Compound A with one or more pharmaceutically acceptable excipients. In another embodiment, there is provided a method of preparing a pharmaceutical composition or administration unit comprising the step of admixing a pharmaceutically acceptable crystalline form of Compound A, characterized by the XRPD pattern of any one of FIGS. 1-9, with one or more pharmaceutically acceptable excipients. In another embodiment, there is provided a method of preparing a pharmaceutical composition or administration unit comprising the step of admixing a pharmaceutically acceptable crystalline form of Compound A, characterized by diffraction data of any one of Tables 1-9, with one or more pharmaceutically acceptable excipients.

In one aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLES

In the following experimental descriptions, the following abbreviations may be used:

| Abbreviation | Meaning |
|---|---|
| CPME | cyclopentyl methyl ether (methoxy cyclopentane) |
| D | day |
| Et | ethyl |
| EtOAc | ethyl acetate |
| h, hr | hour(s) |
| HPLC | high-performance liquid chromatography |
| IPA | isopropyl acetate |
| MCH | methyl cyclohexane |
| Me | methyl |
| MetOAc | methyl acetate |
| MeOH or $CH_3OH$ | methanol |
| 2MeTHF | 2-methyl-tetrahydrofuran |
| MIBK | methyl iso-butyl ketone |
| Min | minute(s) |
| rt or RT | room temperature |
| satd. | saturated |
| TBME | tert-butyl methyl ether |
| XRPD or PXRD | X-ray powder diffraction or powder X-ray diffraction |

Example 1

Compound A (S)-5-benzyl-N-(5-methyl-4-oxo-2,3,4,5-tetrahydrobenzo[b][1,4]oxazepin-3-yl)-4H-1,2,4-triazole-3-carboxamide may be prepared by the methods described in International Patent Application Publication No. WO 2014/125444 (now U.S. patent application Ser. No. 14/763,183), or by methods analogous to those described therein.

Example 2

Compound A—Form 1

(S)-5-Benzyl-N-(5-methyl-4-oxo-2,3,4,5-tetrahydrobenzo[b][1,4]oxazepin-3-yl)-4H-1,2,4-triazole-3-carboxamide (100 mg) was dissolved in 0.9 mL of toluene and 0.1 mL of methylcyclohexane at 60° C., then stirred briskly at room temperature (20° C.) for 4 days. After 4 days, an off-white solid was recovered (76 mg, 76% recovery). The XRPD pattern of this material is shown in FIG. 1 and the corresponding diffraction data is provided in Table 1.

The XRPD analysis was conducted using a PANanalytical X'Pert Pro diffractometer equipped with a copper anode X-ray tube, programmable slits, and X'Celerator detector fitted with a nickel filter. Generator tension and current were set to 45 kV and 40 mA respectively to generate the copper Kα radiation powder diffraction pattern over the range of at least 2-40° 2θ. The test specimen was lightly triturated using an agate mortar and pestle and the resulting fine powder was mounted onto a silicon zero background plate.

TABLE 1

| Diffraction Angle (°2θ) |
|---|
| 5.70 |
| 8.46 |
| 11.46 |
| 16.36 |
| 17.10 |
| 19.82 |

TABLE 1-continued

| Diffraction Angle (°2θ) |
| --- |
| 21.63 |
| 22.03 |
| 23.11 |
| 23.75 |
| 24.35 |
| 24.94 |

Example 3

Compound A—Form 1

A sample of Compound A was dissolved in 4 volumes of MIBK, with brisk stirring and heating to 45° C. If a portion of the sample of Compound A is present as crystalline Form 1, rather than amorphous material, heating to 65-70° C. will be required to completely dissolve the sample, followed by cooling to 45° C. for seeding. In addition, if a clarifying filtration is required, the solution should be maintained at a temperature of 50-60° C. and 0.2 volumes MIBK may be used to rinse, followed by cooling to 45° C. for seeding.

A suspension of 1% wt Form 1 seed crystals in 0.17 volumes MCH is added directly to the Compound A-MIBK solution at 45° C. The container containing the seed crystals may be washed with 0.17 volumes MCH and the additional seed material and MCH added directly to the Compound A recrystallization mixture. The resulting mixture was stirred at 45° C. for one hour, followed by addition of 5.7 volumes of MCH in a slow steady stream or in timed equal aliquots every 15 minutes, over at least 3 hours. The resulting mixture was stirred briskly for 3 hours at 45° C. after the addition of MCH was complete.

The resulting mixture was cooled to about 35° C. at a rate of 0.1-0.25° C./min, then filtered (temperature of mixture should be maintained at >35° C. until filtration is complete). The filter cake was washed with 4 volumes of 4/1 (MCH/MIBK) which had been preheated to 35° C. The crystalline material was dried at 70° C. under vacuum with a nitrogen sweep to provide Compound A in Form 1 in an 80-90% yield, having an XRPD substantially the same as in FIG. 1.

Example 4

Compound A—Methyl Acetate (1:1) Solvate

A sample of Compound A-Form 1 was admixed with methyl-acetate and the resulting mixture was subjected to temperature-cycled ripening between 5-40° C. for 72 hours. The solid material obtained (after filtering and drying) provided the XRPD pattern shown in FIG. 2. The corresponding diffraction data is provided in Table 2.

XRPD diffractograms were acquired using either a Bruker D8 Discovery diffractometer with a HI-STAR GADDS detector or PANalytical X'Pert Pro diffractometer on Si zero-background wafers. All diffractograms were collected using a monochromatic Cu Kα (45 kV/40 mA) radiation and a step size of 0.02°2θ.

TABLE 2

| Diffraction Angle (°2θ) | d-spacing [Å] |
| --- | --- |
| 10.4238 | 8.4868 |
| 10.6954 | 8.2719 |
| 11.0553 | 8.00343 |
| 11.4849 | 7.70496 |
| 13.2805 | 6.667 |
| 15.1819 | 5.83602 |
| 15.4879 | 5.7214 |
| 16.6418 | 5.3272 |
| 18.2579 | 4.85916 |
| 19.6627 | 4.51503 |
| 20.0874 | 4.42053 |
| 20.9768 | 4.23506 |
| 22.2546 | 3.99471 |
| 22.9385 | 3.87714 |
| 23.1494 | 3.84228 |
| 23.4462 | 3.79432 |
| 24.3277 | 3.6588 |
| 24.6278 | 3.61488 |
| 27.0968 | 3.29086 |
| 28.6495 | 3.11594 |
| 30.4083 | 2.93961 |

Example 5

Compound A—Ethyl Acetate (1:1) Solvate

A sample of Compound A-Form 1 was admixed with ethyl-acetate and the resulting mixture was subjected to temperature-cycled ripening between 5-40° C. for 72 hours. The solid material obtained (after filtering and drying) provided the XRPD pattern shown in FIG. 3. The corresponding diffraction data is provided in Table 3. XRPD diffractograms were acquired using the parameters described in Example 4.

TABLE 3

| Diffraction Angle (°2θ) | d-spacing [Å] |
| --- | --- |
| 10.5059 | 8.42069 |
| 10.8457 | 8.15761 |
| 11.515 | 7.68489 |
| 13.0543 | 6.78199 |
| 14.942 | 5.92917 |
| 15.4331 | 5.74159 |
| 16.32 | 5.43152 |
| 18.1075 | 4.89915 |
| 19.3058 | 4.59769 |
| 19.8714 | 4.46809 |
| 20.4154 | 4.35023 |
| 21.8293 | 4.07157 |
| 23.0464 | 3.85923 |
| 23.5371 | 3.77987 |
| 24.1542 | 3.68468 |
| 26.7319 | 3.33494 |
| 28.2478 | 3.15932 |
| 30.0195 | 2.97678 |
| 33.8949 | 2.64477 |

Example 6

Compound A—n-Propyl Acetate (1:0.5) Solvate

Compound A-Form 1 (~50 mg) was dissolved in 10 volumes of n-propyl acetate, then cooled and seeded with a trace of crystalline Compound A-EtOAc solvate. The crystalline material that formed was filtered and dried. This sample was used as n-propyl acetate solvate seed crystals.

Compound A-Form 1 (100 mg) was dissolved in 10 volumes of n-propyl acetate, then cooled and seeded with n-propyl acetate solvate seed crystals. The crystalline material that formed was filtered and dried. The XRPD pattern of this material is shown in FIG. 4 and the corresponding diffraction data is provided in Table 4. XRPD diffractograms were acquired using the parameters described in Example 2.

TABLE 4

| Diffraction Angle (°2θ) |
| --- |
| 4.77 |
| 7.44 |
| 8.38 |
| 10.14 |
| 11.80 |
| 12.18 |
| 13.33 |
| 14.10 |
| 14.96 |
| 16.20 |
| 16.41 |
| 16.84 |

Example 7

Compound A—Iso-Propyl Acetate (1:0.5) Solvate

Compound A-Form 1 (50 mg) was slurried in 2 mL of iso-propyl acetate and seeded with a trace of crystalline Compound A-EtOAc solvate. The crystalline material that formed was isolated by filtration, dried and used as isopropyl acetate solvate seed crystals.

Compound A-Form 1 (100 mg) was slurried in 10 volumes of iso-propyl acetate at RT and seeded with isopropyl acetate solvate seed crystals. The crystalline material that formed was isolated by filtration and dried. The XRPD pattern of this material is shown in FIG. 5 and the corresponding diffraction data is provided in Table 5. XRPD diffractograms were acquired using the parameters described in Example 2.

TABLE 5

| Diffraction Angle (°2θ) |
| --- |
| 4.74 |
| 7.45 |
| 8.31 |
| 10.07 |
| 11.75 |
| 13.28 |
| 14.97 |
| 16.30 |
| 16.71 |
| 16.97 |
| 18.03 |
| 19.05 |

Example 8

Compound A—Ethanol (1:1) Solvate

Compound A-Form 1 (100 mg) was dissolved in 10 volumes of warm ethanol and left to slowly evaporate at RT. After 4 days, the resulting solid was isolated. This sample was used as ethanol solvate seed crystals.

Compound A-Form 1 (100 mg) was suspended in ethanol at RT (using minimal ethanol). Ethanol solvate seed crystals were added and the resulting slurry was stirred for 12 days at RT. The crystalline material that formed was filtered and dried at RT in the filter. The XRPD pattern of this material is shown in FIG. 6 and the corresponding diffraction data is provided in Table 6. XRPD diffractograms were acquired using the parameters described in Example 2.

TABLE 6

| Diffraction Angle (°2θ) |
| --- |
| 4.76 |
| 6.28 |
| 7.37 |
| 8.39 |
| 11.78 |
| 13.33 |
| 14.10 |
| 14.91 |
| 16.44 |
| 16.85 |
| 17.90 |
| 19.01 |

Example 9

Compound A Monohydrate

A sample of Compound A-Form 1 was added to 1:1 MeOH/water, and became an oil. After stirring about 24 hours, the oil solidified into a crystalline solid, which was isolated by vacuum filtration. After drying overnight at 55° C. under vacuum, the crystals showed only water present at 1 mole equivalent. The XRPD pattern of this material is shown in FIG. 7 and the corresponding diffraction data is provided in Table 7. XRPD diffractograms were acquired using the parameters described in Example 2.

TABLE 7

| Diffraction Angle (°2θ) |
| --- |
| 9.03 |
| 9.66 |
| 10.29 |
| 12.29 |
| 13.02 |
| 14.68 |
| 15.11 |
| 17.54 |
| 17.98 |
| 19.45 |
| 20.60 |
| 21.51 |

Example 10

Compound A—Iso-Propyl Alcohol (1:1) Solvate

Compound A-Form 1 (5.5 g) was dissolved in 10 volumes of IPA, with heating (>70° C.) to provide a clear straw color solution. The solution was cooled to ~50° C. over 25 minutes. On cooling to 50° C., white crystalline material self nucleated. The slurry was held at 45-50° C. for 1 hr and then cooled to 20-25° C. over 3 hours. When the temperature reached ~26° C., TBME (10 vols, 55 mLs) was added dropwise. The suspension was held at 20-25° C. overnight. The off-white slurry was filtered in a Buchner and washed with 30 mLs room temp TBME. The recovered solid was dried under vacuum at 55° C. to provide 4.4 g of a white to slightly yellow solid (80% recovery).

The XRPD pattern of this material is shown in FIG. 8 and the corresponding diffraction data is provided in Table 8.

TABLE 8

| Diffraction Angle (°2θ) |
| --- |
| 8.22 |
| 10.35 |
| 12.03 |
| 16.39 |
| 18.69 |
| 19.97 |
| 23.24 |
| 24.64 |
| 26.18 |
| 28.07 |

Example 11

Compound A—Methyl-Isobutyl Ketone Solvate

A 100 mg sample of Compound A was slurried in 10 volumes of 1/1 (vol/vol) MIBK/MCH at 10° C. until sampling, by filtration of a small aliquot, showed a single XRPD pattern. The remaining sample was isolated by filtration and dried under vacuum at 55° C. The XRPD pattern of this material is shown in FIG. 9 and the corresponding diffraction data is provided in Table 9. XRPD diffractograms were acquired using the parameters described in Example 2.

TABLE 9

| Diffraction Angle (°2θ) |
| --- |
| 4.74 |
| 7.51 |
| 8.21 |
| 11.76 |
| 13.30 |
| 13.87 |
| 15.16 |
| 16.22 |
| 17.03 |
| 18.26 |
| 18.95 |
| 19.69 |

Example 12

Compound A—2-Methyl-Tetrahydrofuran (1:0.6) Solvate

Amorphous Compound A (115 mg) was stirred into a 4/1 mixture of 2MeTHF/MCH (1.15 mL). The resulting mixture was heated to dissolve Compound A, then cooled to RT. At RT, 0.3 mL of MCH was added dropwise to promote solid formation. The resulting solids were isolated after 4 days. The XRPD pattern of this material is shown in FIG. 10 and the corresponding diffraction data is provided in Table 10. XRPD diffractograms were acquired using the parameters described in Example 2.

TABLE 10

| Diffraction Angle (°2θ) |
| --- |
| 4.73 |
| 7.50 |
| 8.25 |
| 11.72 |
| 12.34 |
| 13.14 |

TABLE 10-continued

| Diffraction Angle (°2θ) |
| --- |
| 13.53 |
| 15.02 |
| 15.92 |
| 16.16 |
| 16.55 |
| 16.89 |

Example 13

Compound A—Dimethylcarbonate (1:1) Solvate

A sample of Compound A-Form 1 was admixed with dimethylcarbonate and the resulting mixture was subjected to temperature-cycled ripening between 5-40° C. for 72 hours. The solid material obtained (after filtering and drying) provided the XRPD pattern shown in FIG. 11. The corresponding diffraction data is provided in Table 11. XRPD diffractograms were acquired using the parameters described in Example 4.

TABLE 11

| Diffraction Angle (°2θ) | d-spacing [Å] |
| --- | --- |
| 10.6883 | 8.27735 |
| 13.2375 | 6.68857 |
| 15.0286 | 5.89521 |
| 15.5779 | 5.68853 |
| 16.0784 | 5.51259 |
| 18.1619 | 4.88461 |
| 19.2597 | 4.6086 |
| 20.35 | 4.36408 |
| 21.5003 | 4.13312 |
| 21.8806 | 4.06214 |
| 23.1232 | 3.84658 |
| 23.5786 | 3.7733 |
| 23.831 | 3.73392 |
| 24.3735 | 3.65202 |
| 24.8869 | 3.57783 |
| 26.8243 | 3.32366 |
| 28.4543 | 3.13687 |
| 32.5432 | 2.75147 |
| 34.2899 | 2.6152 |

Example 14

Compound A—Methoxy-Cyclopentane (1:0.5) Solvate

Compound A-Form 1 (100 mg) was added to 5 volumes CPME, which formed a gum. This mixture was stirred for 3 days, after which time a solid had formed. The solid was vacuum filtered and dried in the filter at RT. The XRPD pattern of this material is shown in FIG. 12 and the corresponding diffraction data is provided in Table 12. XRPD diffractograms were acquired using the parameters described in Example 2.

TABLE 12

| Diffraction Angle (°2θ) |
| --- |
| 4.71 |
| 7.38 |
| 8.29 |
| 11.70 |
| 11.82 |

TABLE 12-continued

| Diffraction Angle (°2θ) |
| --- |
| 13.04 |
| 13.53 |
| 14.85 |
| 15.77 |
| 16.24 |
| 16.68 |
| 17.89 |

What is claimed is:

1. A crystalline form of a compound represented by:

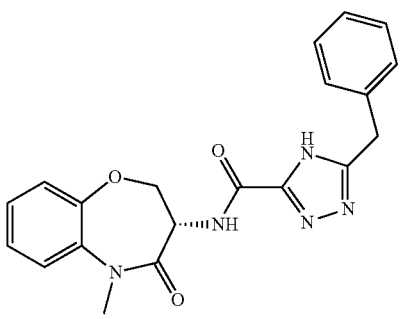 [SMILES: CN1C(=O)[C@@H](NC(=O)c2nnc(Cc3ccccc3)[nH]2)COc2ccccc21]

wherein the crystalline form is a crystalline solvate of the compound and the crystalline solvate is selected from the group consisting of a methyl acetate, n-propyl acetate, isopropyl acetate, water, iso-propyl alcohol, methyl-isobutylketone, 2-methyl-tetrahydrofuran, dimethyl carbonate, and methoxy-cyclopentane solvate of the compound, wherein the water solvate is a monohydrate.

2. The crystalline form according to claim 1, wherein the crystalline solvate is a methyl acetate solvate, and wherein the crystalline form is characterized by an X-ray powder diffraction pattern substantially in accordance with FIG. 2.

3. The crystalline form according to claim 1, wherein the crystalline solvate is a methyl acetate solvate, and wherein the crystalline form is characterized by diffraction data substantially in accordance with the following:

| Diffraction Angle (°2θ) | d-spacing [Å] |
| --- | --- |
| 10.4238 | 8.4868 |
| 10.6954 | 8.2719 |
| 11.0553 | 8.00343 |
| 11.4849 | 7.70496 |
| 13.2805 | 6.667 |
| 15.1819 | 5.83602 |
| 15.4879 | 5.7214 |
| 16.6418 | 5.3272 |
| 18.2579 | 4.85916 |
| 19.6627 | 4.51503 |
| 20.0874 | 4.42053 |
| 20.9768 | 4.23506 |
| 22.2546 | 3.99471 |
| 22.9385 | 3.87714 |
| 23.1494 | 3.84228 |
| 23.4462 | 3.79432 |
| 24.3277 | 3.6588 |
| 24.6278 | 3.61488 |
| 27.0968 | 3.29086 |
| 28.6495 | 3.11594 |
| 30.4083 | 2.93961 |

4. The crystalline form according to claim 1, wherein the crystalline solvate is an n-propyl acetate solvate, and wherein the crystalline form is characterized by an X-ray powder diffraction pattern substantially in accordance with FIG. 4.

5. The crystalline form according to claim 1, wherein the crystalline solvate is an n-propyl acetate solvate, and wherein the crystalline form is characterized by diffraction angle data substantially in accordance with the following: 4.77, 7.44, 8.38, 10.14, 11.80, 12.18, 13.33, 14.10, 14.96, 16.20, 16.41, 16.84 (°2θ).

6. The crystalline form according to claim 1, wherein the crystalline solvate is an isopropyl acetate solvate, and wherein the crystalline form is characterized by an X-ray powder diffraction pattern substantially in accordance with FIG. 5.

7. The crystalline form according to claim 1, wherein the crystalline solvate is an isopropyl acetate solvate, and wherein the crystalline form is characterized by diffraction angle data substantially in accordance with the following: 4.74, 7.45, 8.31, 10.07, 11.75, 13.28, 14.97, 16.30, 16.71, 16.97, 18.03, 19.05 (°2θ).

8. The crystalline form according to claim 1, wherein the crystalline solvate is a monohydrate, and wherein the crystalline form is characterized by an X-ray powder diffraction pattern substantially in accordance with FIG. 7.

9. The crystalline form according to claim 1, wherein the crystalline solvate is a monohydrate, and wherein the crystalline form is characterized by diffraction angle data substantially in accordance with the following: 9.03, 9.66, 10.29, 12.29, 13.02, 14.68, 15.11, 17.54, 17.98. 19.45, 20.60, 21.51 (°2θ).

10. The crystalline form according to claim 1, wherein the crystalline solvate is an isopropyl alcohol solvate, and wherein the crystalline form is characterized by an X-ray powder diffraction pattern substantially in accordance with FIG. 8.

11. The crystalline form according to claim 1, wherein the crystalline solvate is an isopropyl alcohol solvate, and wherein the crystalline form is characterized by diffraction angle data substantially in accordance with the following: 8.22, 10.35, 12.03, 16.39, 18.69, 19.97, 23.24, 24.64, 26.18, 28.07 (°2θ).

12. The crystalline form according to claim 1, wherein the crystalline solvate is a methyl-isobutyl ketone solvate, and wherein the crystalline form is characterized by an X-ray powder diffraction pattern substantially in accordance with FIG. 9.

13. The crystalline form according to claim 1, wherein the crystalline solvate is a methyl-isobutyl ketone solvate, and wherein the crystalline form is characterized by diffraction angle data substantially in accordance with the following: 4.74, 7.51, 8.21, 11.76, 13.30, 13.87, 15.16, 16.22, 17.03, 18.26, 18.95, 19.69 (°2θ).

14. The crystalline form according to claim 1, wherein the crystalline solvate is a 2-methyl-tetrahydrofuran solvate, and wherein the crystalline form is characterized by an X-ray powder diffraction pattern substantially in accordance with FIG. 10.

15. The crystalline form according to claim 1, wherein the crystalline solvate is a 2-methyl-tetrahydrofuran solvate, and wherein the crystalline form is characterized by diffraction angle data substantially in accordance with the following: 4.73, 7.50, 8.25, 11.72, 12.34, 13.14, 13.53, 15.02, 15.92, 16.16, 16.55, 16.89 (°2θ).

16. The crystalline form according to claim 1, wherein the crystalline solvate is a dimethyl carbonate solvate, and wherein the crystalline form is characterized by an X-ray powder diffraction pattern substantially in accordance with FIG. 11.

17. The crystalline form according to claim 1, wherein the crystalline solvate is a dimethyl carbonate solvate, and wherein the crystalline form is characterized by diffraction data substantially in accordance with the following:

| Diffraction Angle (°2θ) | d-spacing [Å] |
|---|---|
| 10.6883 | 8.27735 |
| 13.2375 | 6.68857 |
| 15.0286 | 5.89521 |
| 15.5779 | 5.68853 |
| 16.0784 | 5.51259 |
| 18.1619 | 4.88461 |
| 19.2597 | 4.6086 |
| 20.35 | 4.36408 |
| 21.5003 | 4.13312 |
| 21.8806 | 4.06214 |
| 23.1232 | 3.84658 |
| 23.5786 | 3.7733 |
| 23.831 | 3.73392 |
| 24.3735 | 3.65202 |
| 24.8869 | 3.57783 |
| 26.8243 | 3.32366 |
| 28.4543 | 3.13687 |
| 32.5432 | 2.75147 |
| 34.2899 | 2.6152. |

18. The crystalline form according to claim 1, wherein the crystalline solvate is a methoxy-cyclopentane solvate, and wherein the crystalline form is characterized by an X-ray powder diffraction pattern substantially in accordance with FIG. 12.

19. The crystalline form according to claim 1, wherein the crystalline solvate is a methoxy-cyclopentane solvate, and wherein the crystalline form is characterized by diffraction angle data substantially in accordance with the following: 4.71, 7.38, 8.29, 11.70, 11.82, 13.04, 13.53, 14.85, 15.77, 16.24, 16.68, 17.89 (°2θ).

* * * * *